United States Patent [19]

Dewald et al.

[11] Patent Number: 4,946,652

[45] Date of Patent: Aug. 7, 1990

[54] CHEMICAL ANALYSIS PROBE STATION

[75] Inventors: Lamar R. Dewald; William E. Ryan, both of Antioch, Calif.

[73] Assignee: The Dow Chemical Company, Midland, Mich.

[21] Appl. No.: 139,510

[22] Filed: Dec. 30, 1987

[51] Int. Cl.$^5$ .............................................. B01L 9/04
[52] U.S. Cl. ................................... 422/104; 248/284; 250/227.11; 350/250; 422/99; 436/163
[58] Field of Search ............... 422/99, 100, 102, 104; 436/180, 163; 248/284; 350/250; 250/227; 356/409, 412

[56] References Cited

U.S. PATENT DOCUMENTS

| | | | |
|---|---|---|---|
| 1,353,500 | 9/1920 | Spindler | 422/68 X |
| 2,653,071 | 9/1953 | Lundstrom | 248/284 |
| 2,902,349 | 9/1959 | Berner | 422/104 |
| 3,026,182 | 3/1962 | Jankowski et al. | 356/412 X |
| 3,197,285 | 7/1965 | Rosen | 422/100 |
| 3,389,835 | 6/1968 | Marbach et al. | 422/100 |
| 3,417,953 | 12/1968 | Hillquist et al. | 248/284 |
| 3,426,190 | 2/1969 | Bobrick | 248/284 |
| 3,756,783 | 9/1973 | Williams | 356/409 X |
| 3,842,680 | 10/1974 | Vollick et al. | 422/100 X |
| 3,905,573 | 9/1975 | Davis | 248/284 |
| 4,000,973 | 1/1977 | Petersen | 436/180 X |
| 4,064,737 | 12/1979 | Sieverin | 422/104 X |
| 4,240,751 | 12/1980 | Linnecke et al. | 356/409 |
| 4,343,766 | 8/1982 | Sisti et al. | 422/100 X |
| 4,347,215 | 8/1982 | Sisti et al. | 422/100 X |
| 4,356,722 | 11/1982 | Bunce et al. | 422/68 X |
| 4,495,149 | 1/1985 | Iwata et al. | 422/63 X |
| 4,712,313 | 12/1987 | Gettleman | 248/284 |

OTHER PUBLICATIONS

Whatman Catalog, Fall 1986, New Instrumentation & Lab Equipment, p. 13.
VWR Scientific Apparatus Catalog 1984/1985, p. 1027.

*Primary Examiner*—Michael S. Marcus
*Assistant Examiner*—Amalia L. Santiago
*Attorney, Agent, or Firm*—Timothy S. Stevens

[57] ABSTRACT

Apparatus for selectively and precisely placing a chemical analysis probe (such as a fiber optic probe): (1) in a liquid sample contained in an open-mouthed sample vessel positioned on a sample support, or (2) in a wash collection chamber. Any residual sample remaining on the probe can be washed from it with a stream of volatile wash liquid when the probe is in the wash collection chamber and jets of gas can be directed onto the washed probe to speed the evaporation of any residual wash liquid from the probe. A latch can be used to hold the probe in the wash collection chamber. In one embodiment, four parallel two-ended link members are used, each of which are pivotally attached at one end thereof to a stationary portion of the station and each of which are pivotally attached at the other end thereof to a movable portion of the station, the probe being attached to the movable portion of the station so that the probe can be moved along a predetermined path from a position within the collection chamber to a precise position of immersion in the sample and at a later time back to a position within the collection chamber.

1 Claim, 2 Drawing Sheets

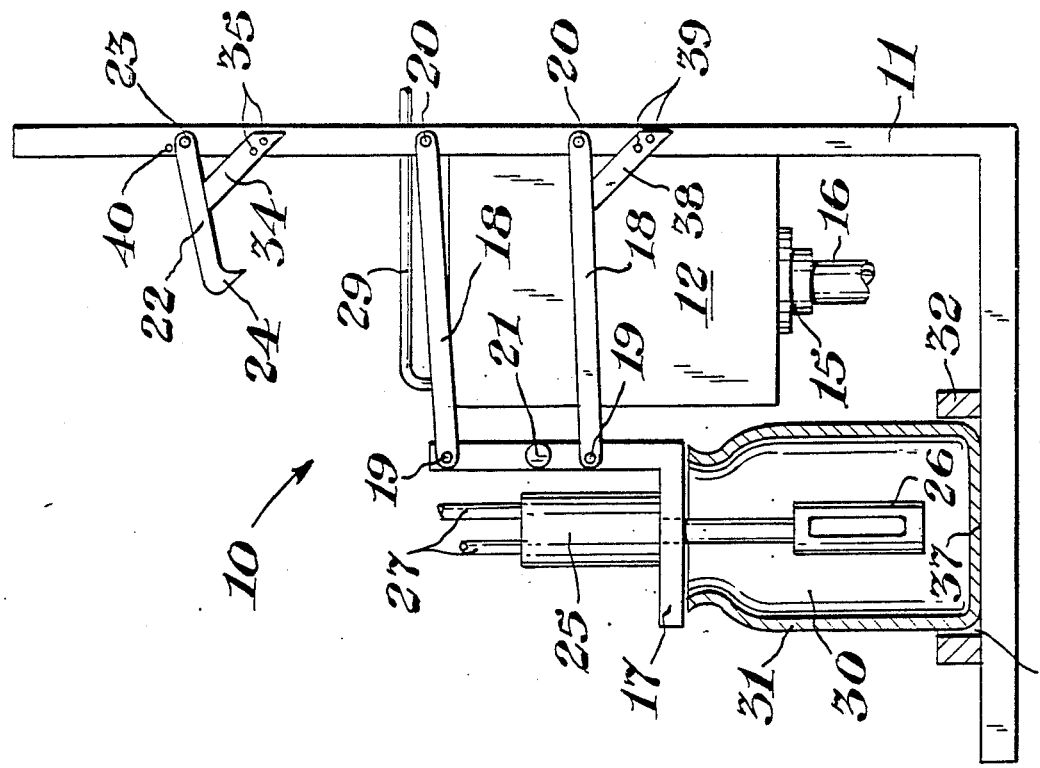
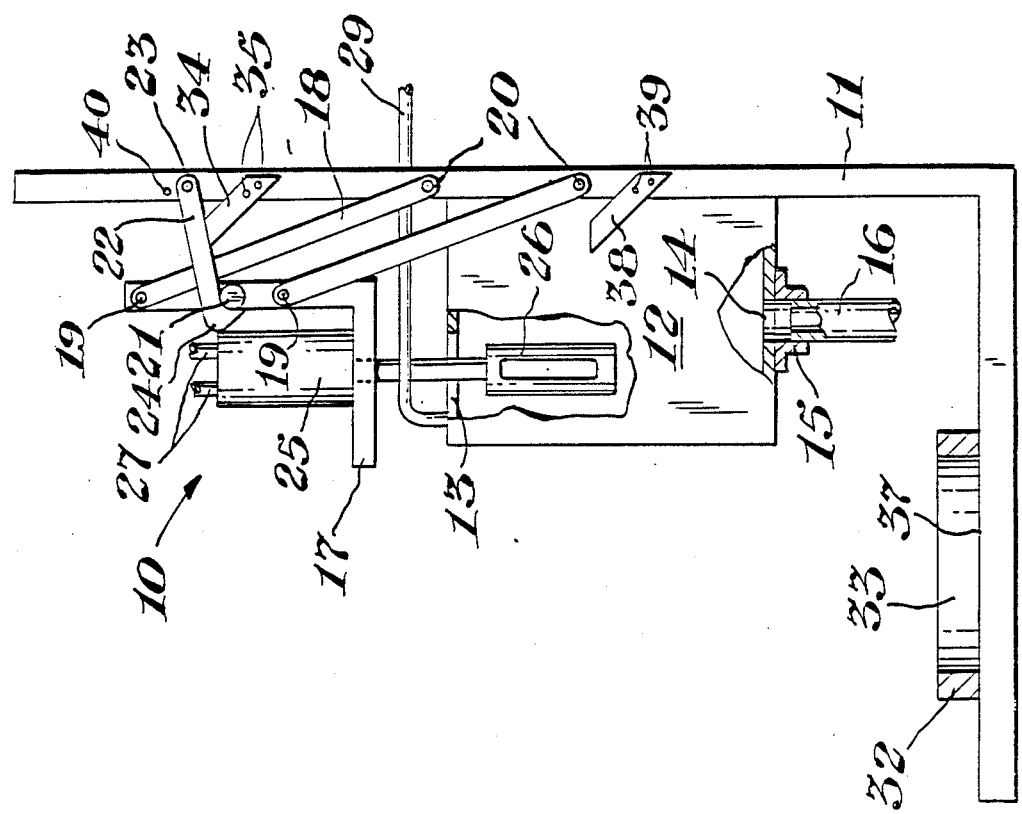

CHEMICAL ANALYSIS PROBE STATION

FIELD OF THE INVENTION

The invention is in the field of apparatus used in chemical analysis. More specifically, the invention relates to apparatus for holding, positioning and washing a chemical analysis probe.

BACKGROUND OF THE INVENTION

Chemical analysis probes, such as pH probes, ion-specific electrodes and fiber optic probes, are widely used to chemically analyze samples, usually liquid samples contained in a sample vessel. When the probe is a fiber optic probe, light can be directed down a fiber optic cable to the fiber optic probe, is then directed through the sample to a mirror, then bounces off of the mirror back through the sample and then back up another fiber optic cable to a photometer. The sample absorbs a portion of the light so directed through it and this absorption is measured to analyze the sample.

The probe is generally supported and positioned by apparatus which allows the immersion of the probe into the sample where it is held during the analysis. Then, generally, the probe is removed from the sample and any residual sample remaining on the probe is washed away with a suitable liquid. In the case of a fiber optic probe the wash liquid is frequently a volatile liquid. Generally, the probe is supported and positioned by an arm vertically movable along a vertical column or by an arm comprising link members which provide for horizontal as well as vertical movement. When chemical analysis probes are used for routine analyses by unskilled persons (such as by an industrial worker who may be more used to operating rugged process valves than more fragile laboratory equipment), the known probe supports either provide too little freedom of movement of the probe or too much. Care is needed to guide the probe into the sample (generally a two-handed operation) without bumping the probe or probe arm into the sample vessel with the possibility for breaking the probe and/or the vessel. In addition, contamination of the sample can be a problem if a washed probe is used for another analysis before the wash liquid has completely evaporated.

SUMMARY OF THE INVENTION

The invention is a chemical analysis probe station suitable for use by unskilled persons. The invention comprises means for selectively placing a probe in a precise first position and in a spacially different precise second position relative to a sample support, so that the probe can be immersed into a sample positioned at the sample support when the probe is placed in the precise second position, and means for collecting a liquid used to wash the probe when the probe is placed in the precise first position, so that any residual sample remaining on the probe when the probe is placed from the precise second position to the precise first position can be washed from the probe by a wash liquid and collected. The means for selectively placing a fiber optic probe in a precise first position and in a spacially different precise second position can comprise four two-ended link members, each of which is pivotally attached at one end thereof to a stationary portion of the station and each of which is pivotally attached at the other end thereof to a movable portion of the station, the probe being attached to the movable portion of the station which is preferably limited in its travel by a mechanical stop so that the movable portion of the station does not hit a sample vessel positioned at the sample support. The means for collecting a liquid used to wash the probe when the probe is placed in the precise first position comprises an open-mouthed container having an additional drain opening at the bottom of the container, so that when the probe is placed from the precise second position to the precise first position, the probe passes through the open mouth of the container and can be washed with a liquid, the liquid being collected by the container and drained from the container through the opening at the bottom of the container.

The probe station can further comprise means for directing a stream of gas onto the probe when the probe is placed in the precise first position so that any volatile residual wash liquid remaining on the probe will evaporate at a faster rate. In addition, the invention can also comprise a means for latching in the precise first position the means for placing a chemical analysis probe in a precise first position and in a spacially different precise second position. The invention can also comprise a means for positioning an open-mouthed sample holding vessel on the sample support, so that when the probe is placed from the precise first position to the precise second position and the vessel is filled with a sample, the probe passes through the open mouth of the sample holding vessel and is immersed in the sample.

BRIEF DESCRIPTION OF THE DRAWINGS

FIG. 1 is a side view, mostly in full and partly broken away and in section, of a probe station of the present invention showing the distal end of a fiber optic probe within an open-mouthed probe wash collection container, i.e., with the fiber optic probe in the precise first position.

FIG. 2 shows a side view, mostly in full and partly in section, of the probe station of FIG. 1 with the distal end of the fiber optic probe shown immersed in a sample which is contained in a sample vessel, i.e., with the fiber optic probe shown in the precise second position

DETAILED DESCRIPTION OF THE INVENTION

Figure 3:
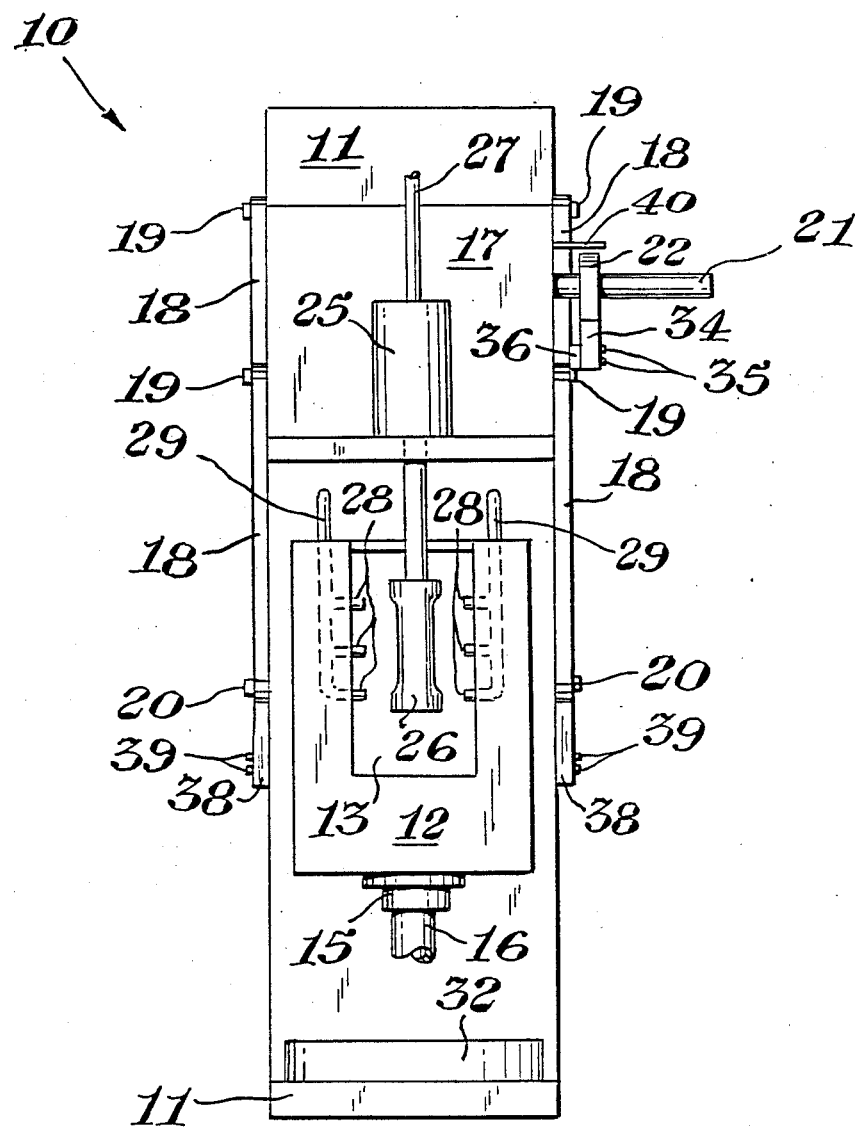
FIG. 3 is a front view of the open-mouthed wash collection container of the probe station of FIG. 1 showing an array of jets each directing a stream of gas onto the probe placed in the precise first position as shown in FIG. 1.

Referring now to FIGS. 1 and 3, therein is shown a chemical analysis probe station 10 of the present invention. The probe station 10 includes a base 11 having attached thereto a wash collection box 12. The wash collection box 12 has an open mouth 13 which is better viewed in FIG. 3. The wash collection box 12 additionally has a drain opening 14 positioned at the bottom of the wash collection box 12. Aligned with the drain opening 14 is a pipe fitting 15. A drain pipe 16 is shown connected to the flange 15. An L-shaped bracket 17 is shown attached to the base 11 by four two-ended link members 18 which are preferably lightened by multiple holes therethrough, not shown. One end of each link member 18 is attached to the L-shaped bracket 17 by shoulder bolts 19. The other end of the link members 18 is attached to the base 11 by shoulder bolts 20. A handle 21 is shown attached to the L-shaped bracket 17. An L-shaped hook member 22 is shown pivotally attached to the base 11 by a shoulder bolt 23. The hook end 24 of the L-shaped hook member 22 is shown engaged with the handle 21 and thereby holding the L-shaped bracket 17 in the position shown in FIGS. 1 and 3 (a magnetic latch, or a pinch latch or other means could have been used but the hook member 22 works well). A fiber optic probe 25 is shown attached to the L-shaped bracket 17 with the distal end 26 of the probe 25 shown extended through the L-shaped bracket 17 and inside the wash collection box 12, i.e., in the precise first position. A pair of fiber optic cables 27 is shown attached to the fiber optic probe 25. A series of gas jets 28 is shown connected to gas pipes 29 so that a gas, usually nitrogen, flowed into the gas pipes 29 is directed through the jets 28 onto the distal end 26 of the probe 25, i.e. the jets 28 are directed inwardly of the box 12 at the distal end 26 of the probe 25.

Now referring particularly to FIG. 2, therein is shown a side view of the embodiment of the invention shown in FIG. 1 with the fiber optic probe 25 and L-shaped bracket 17 swung downwardly into the position shown. The distal end 26 of the probe 25 is shown immersed in a liquid sample 30 which is contained in a sample vessel 31 which is shown in section. The vessel 31 is shown positioned by a body 32 which defines a centrally located cavity 33 so that the bottom of the vessel 31 fits closely within it. The L-shaped hook member 22 is supported in a generally horizontal position by a support 34 which is attached to the base 11 by bolts 35 which pass to the base 11 through a spacer 36 (shown in FIG. 3). A set of supports 38 are attached to the base 11 by bolts 39 so that the bottom of the L-shaped bracket 17 stops precisely and before contacting the vessel 31 (and possibly breaking the vessel 31). In addition, the length of the link members 18 and their position of attachment to the base 11 and the bracket 17 determine the arc described by the distal end 26 of the probe 25 so that it passes through the mouth of the vessel 31 without hitting it (and possibly breaking the vessel 31 or damaging the probe 25).

In operation, a vessel 31 is filled with sample 30 and placed within the body 32 on a sample support 37. The right hand is placed on the handle 21 and the L-shaped hook member 22 is pressed upwardly with the right thumb to unlatch the handle 21 thereby allowing the handle 21 to be pulled forward and downward from the position shown in FIG. 1 to that shown in FIG. 2. The fiber optic probe is then used in an analysis of the sample 30 in the conventional manner and then the right hand is placed again on the handle 21 and the handle 21 is moved upward and rearward to the position shown in FIG. 1 with the L-shaped hook member 22 automatically latching the handle 21 as shown in FIG. 1. A pin 40 prevents the hook member 22 from spinning around on the bolt 25 if the handle 21 is moved upwardly rapidly. In the position shown in FIG. 3, a suitable stream of liquid is directed onto the distal end 26 of the fiber optic probe 25 to wash away any residual sample 30 remaining on the distal end 26 of the probe 25. The excess wash liquid will drain into the interior of the wash collection box 12 and drain through the opening 14 into the drain pipe 16 which flows to a waste collection bottle not shown. Preferably, a gas is flowed into the gas pipes 29 to direct a stream of gas through the jets 28 onto the distal end 26 of the probe 25 so that the residual wash liquid remaining on the distal end 26 of the probe 25 is evaporated therefrom at a rate which is accelerated relative to the rate of evaporation that occurs without the use of jets of gas directed onto the distal end 26 of the probe 25. The vapors can be vented through the pipe 16 if desired. The probe station is now in condition for analysis of another sample. By its nature, the station 10 essentially does not allow sidewise movement of the probe 25 and provides for precise positioning of the probe at two spacially different positions. Therefore, a sample vessel 31 positioned in the cavity 33 on the sample support 37 is always in alignment with the probe 25 when it is placed into the precise second position. This feature of the station 10 is especially appreciated by unskilled users. It should be understood that a vessel 31 of appropriate dimensions should be used so that the distal end 26 of the probe 25 will enter the vessel 31.

The specific probe 25 used is not critical to the present invention, e.g., the probe need not incorporate a mirror, can be a pH probe or other chemical analysis probe. A specific example of a suitable fiber optic probe 25 is the 6-to-1 Vis-NIR probe made by Guided Wave Corporation, Inc. of California, which can be connected to a Spectrum Analyzer, also sold by the Guided Wave Corporation. The collection box 12 is preferably made from filled Teflon ® brand plastic. Preferably, the remainder of the probe station 10 is made of stainless steel or other corrosion-resistant material. The link members 18 are comprised by but one means for positioning the probe. The probe 25 could have been positioned by a system comprising a guide track and track followers, by a pivoted pneumatic cylinder or almost any other suitable means otherwise meeting the objectives of the present invention. The probe station 10 is but one embodiment of the present invention of which there are many.

What is claimed is:

1. An analytical chemistry probe station suitable for use by unskilled persons, comprising:
   a sample support;
   a chemical analysis probe;
   means for selectively placing the chemical analysis probe in a precise first position and in a spacially different precise second position relative to the sample support, so that the probe can be immersed into a sample positioned at the sample support when the probe is placed in the precise second position, the means for selectively placing the chemical analysis probe in said precise first position and in said spacially different precise second position comprising four two-ended link members each of which is pivotally attached at one end thereof to a stationary portion of the station and each of which is pivotally attached at the other end thereof to a movable portion of the station, the probe being attached to the movable portion of the station;
   means for collecting a liquid used to wash the probe when the probe is placed in the precise first position, so that any residual sample remaining on he probe when the probe is placed from the second position tot he first position can be washed from the probe by a wash liquid and collected; and
   means for latching in the precise first position the means for placing the chemical analysis probe in said precise first position and in a spacially different precise second position, the means for latching comprising a pre-formed L-shaped hook member, the shank end of which is pivotally attached to the stationary portion of the station, the hook end of which engages a handle attached to the movable portion of the station when the probe is positioned in the precise first position, so that the probe is latched in the precise first position.

* * * * *